US010060914B2

(12) United States Patent
Castella et al.

(10) Patent No.: US 10,060,914 B2
(45) Date of Patent: Aug. 28, 2018

(54) METHODS FOR SEPARATING CELLS

(71) Applicant: CENTRE HOSPITALIER UNIVERSITAIRE VAUDOIS (C.H.U.V.), Lausanne (CH)

(72) Inventors: Vincent Castella, Le Mont-sur-Lausanne (CH); Frédéric Grosjean, Aubonne (CH)

(73) Assignee: CENTRE HOSPITALIER UNIVERSITAIRE VAUDOIS, Lausanne (CH)

( * ) Notice: Subject to any disclaimer, the term of this patent is extended or adjusted under 35 U.S.C. 154(b) by 0 days.

(21) Appl. No.: 15/317,494

(22) PCT Filed: Jun. 9, 2015

(86) PCT No.: PCT/EP2015/062838
§ 371 (c)(1),
(2) Date: Dec. 9, 2016

(87) PCT Pub. No.: WO2015/189208
PCT Pub. Date: Dec. 17, 2015

(65) Prior Publication Data
US 2017/0115282 A1    Apr. 27, 2017

(30) Foreign Application Priority Data
Jun. 11, 2014   (EP) .................................... 14171937

(51) Int. Cl.
*G01N 33/543*      (2006.01)

(52) U.S. Cl.
CPC ................. *G01N 33/54326* (2013.01); *G01N 2333/70592* (2013.01)

(58) Field of Classification Search
None
See application file for complete search history.

(56) References Cited

U.S. PATENT DOCUMENTS

| | | | |
|---|---|---|---|
| 4,230,685 A | 10/1980 | Senyei et al. | |
| 4,452,773 A | 6/1984 | Molday | |
| 4,770,183 A | 9/1988 | Groman et al. | |
| 5,385,707 A | 1/1995 | Miltenyi et al. | |
| 5,411,863 A | 5/1995 | Miltenyi | |
| 5,543,289 A | 8/1996 | Miltenyi | |
| 5,693,539 A | 12/1997 | Miltenyi et al. | |

FOREIGN PATENT DOCUMENTS

| | | | |
|---|---|---|---|
| WO | WO-1985004330 A1 | 10/1985 | |
| WO | WO-1990007380 A2 | 7/1990 | |
| WO | WO-0077251 A2 | 12/2000 | |
| WO | WO-0119956 A2 | 3/2001 | |
| WO | WO 01/35759 * | 5/2001 | ............... A23J 1/00 |

OTHER PUBLICATIONS

The Masters' Theses by Elyse Cooper, Boston University, 2011; 89 pages total. (Year: 2011).*
Lounsbury, Jenny A., et al: "Enhanced recovery of spermatozoa and comprehensive lysis of epithelial cells from sexual assault samples having a low cell counts or aged up to one year", Forensic Science International: Genetics Elsevier BV, Netherlands, vol. 8, No. 1, Jan. 1, 2014 (Jan. 1, 2014), pp. 84-89.
Miltenyi, S., et al: "High Gradient Magnetic Cell Separation With Macs", Cytometry, Alan Liss, New York, US, vol. 11, No. 11, Jan. 1, 1990 (Jan. 1, 1990), pp. 231-238.
Tsutsumi, Hirofumi, et al: "A case of personal identification due to detection of rare DNA types from seminal stain", Journal of Oral Science, vol. 51, No. 4, Jan. 1, 2009 (Jan. 1, 2009), pp. 645-650.
Diekman, A. B., et al: "N-linked glycan of a sperm CD52 glycoform associated with human infertility", The FASEB Journal, Federation of American Societies for Experimental Biology, Bethesda, US, vol. 13, No. 11, Aug. 1, 1999 (Aug. 1, 1999), pp. 1303-1313.
International Search Report and Written Opinion of the International Searching Authority issued in PCT/EP2015/062838, dated Aug. 20, 2015; ISA/EP.
International Preliminary Report on Patentability (Chapter II) issued in PCT/EP2015/062838, dated Sep. 26, 2016; IPEA/EP.

* cited by examiner

*Primary Examiner* — Christina M Borgeest
(74) *Attorney, Agent, or Firm* — Harness, Dickey and Pierce, P.L.C.

(57) ABSTRACT

The invention is in the field of analysis of cell populations and cell separation and the compositions obtained thereby. More particularly, the invention concerns a method for separating cells of interest according to a specific marker expressed on their surface.

22 Claims, 10 Drawing Sheets

Propidium iodide

METHODS FOR SEPARATING CELLS

PRIORITY STATEMENT

This patent application is a U.S. national stage filing under 35 U.S.C. § 371 of International Application No. PCT/EP2015/062838, filed on 9 Jun. 2015, which claims priority to European Patent Application No. 14171937.7, filed on 11 Jun. 2014. The entire disclosures of each of the above recited applications are incorporated herein by reference.

FIELD OF THE INVENTION

The invention is in the field of analysis of cell populations and cell separation and the compositions obtained thereby. More particularly, the invention concerns a method for separating cells of interest according to a specific marker expressed on their surface.

BACKGROUND OF THE INVENTION

Biological samples from a crime scene often contain a mixture of various cell from more than one person. For example, Swabs obtained for identification of perpetrator in sexual aggression contains a mix of both victim and aggressor cells, with a large number of the cells originating from the victim (epithelial cells, . . . ).

Thus, there are many situations when various kind of biological material can be collected. In view of the above, there is a need to develop an improved method for efficiently separating cells of interest according to a specific marker expressed on their surface when said cells are in a dry state form of a plurality of cells contained on an inert substrate.

SUMMARY OF THE INVENTION

The present invention concerns a method for separating spermatozoa according to the specific marker CD52 (Human epididymal secreted protein) expressed on their surface from a plurality of cells contained, in a dry state, on an inert substrate, which method comprises the steps of
  i) obtaining the plurality of cells contained on the inert substrate,
  ii) contacting said plurality of cells with a serum-free buffer comprising Phosphate buffered saline 1× and about 2-20 mM of EDTA, at about 10-30° C. during 10-45 min and exposing the plurality of cells to at least one magnetic particle under conditions effective to allow the direct or indirect coupling of the magnetic particle to the specific marker CD52 expressed on the surface of the spermatozoa,
  iii) recovering the plurality of cells and
  iv) separating the spermatozoa that are coupled to the magnetic particle from the cells not coupled to the magnetic particle.

A further object of the present invention is to provide a method for enriching cells in spermatozoa according to the specific marker CD52 (Human epididymal secreted protein) expressed on their surface from a plurality of cells contained, in a dry state, on an inert substrate, which method comprises the steps of
  i) obtaining the plurality of cells contained on the inert substrate,
  ii) contacting said plurality of cells with a serum-free buffer comprising Phosphate buffered saline 1× and about 2-20 mM of EDTA, at about 10-30° C. during 10-45 min and exposing the plurality of cells to at least one magnetic particle under conditions effective to allow the direct or indirect coupling of the magnetic particle to the specific marker CD52 expressed on the surface of the spermatozoa,
  iii) recovering the plurality of cells and
  iv) separating the spermatozoa that are coupled to the magnetic particle from the cells not coupled to the magnetic particle.

Another object concerns a kit, as well as its use, for practicing one or more methods of the invention comprising one or more reagents, one or more magnetic particle, one or more binding partner and/or instructions for use.

A magnetic particle labeled with a binding partner that specifically binds to a marker CD52 expressed on the surface of the spermatozoa is also an object of the present invention.

DESCRIPTION

Although methods and materials similar or equivalent to those described herein can be used in the practice or testing of the present invention, suitable methods and materials are described below. All publications, patent applications, patents, and other references mentioned herein are incorporated by reference in their entirety. The publications and applications discussed herein are provided solely for their disclosure prior to the filing date of the present application. Nothing herein is to be construed as an admission that the present invention is not entitled to antedate such publication by virtue of prior invention. In addition, the materials, methods, and examples are illustrative only and are not intended to be limiting.

In the case of conflict, the present specification, including definitions, will control. Unless defined otherwise, all technical and scientific terms used herein have the same meaning as is commonly understood by one of skill in art to which the subject matter herein belongs. As used herein, the following definitions are supplied in order to facilitate the understanding of the present invention.

The term "comprise/comprising" is generally used in the sense of include/including, that is to say permitting the presence of one or more features or components. The terms "comprise" and "comprising" also encompass the more restricted ones "consist" and "consisting".

As used in the specification and claims, the singular form "a", "an" and "the" include plural references unless the context clearly dictates otherwise.

The terms "conjugated", "attached", and "linked" (and similar terms, e.g. "conjugation," "attachment," and "linkage") are used interchangeably herein to refer to a chemical association of two molecules, e.g., a nucleic acid molecule and a polypeptide. The chemical association may be covalent or non-covalent. The two molecules can be linked directly, or indirectly, e.g., via a linker ("spacer") molecule, a solid support, and the like.

The term "about" indicates a defined range around that value. If "X" were the value, "about X" would generally indicate a value from 0.90× to 1.1 OX. Any reference to "about X" minimally indicates at least the values X, 0.90X, 0.9 IX, 0.92X, 0.93X, 0.94X, 0.95X, 0.96X, 0.97X, 0.98X, 0.99X, 1.01X, 1.02X, 1.03X, 1.04X, 1.05X, 1.06X, 1.07X, 1.08X, 1.09X, and 1.10X. Thus, "about X" is intended to disclose, e.g., "0.98X." When "about" is applied to the beginning of a numerical range, it applies to both ends of the range. Thus, "from about 6 to 8.5" or "from about 6-8.5" is equivalent to "from about 6 to about 8.5." When "about" is applied to the first value of a set of values, it applies to all values in that set. Thus, "about 7, 9, or 11%" is equivalent to "about 7%, about 9%, or about 11%."

The present invention thus relates to a method for separating spermatozoa according to the specific marker CD52 (Human epididymal secreted protein) expressed on their surface from a plurality of cells contained, in a dry state, on an inert substrate This method presents the advantage of avoiding any partial lysis before the physical separation of the cellular input from the contributors, thus preventing potential alteration of the DNA of spermatozoa within cells with compromised membrane integrity.

The method generally comprises the steps of
i) obtaining the plurality of cells contained on the inert substrate,
ii) contacting said plurality of cells with a serum-free buffer comprising Phosphate buffered saline 1× and about 2-20 mM of EDTA, at about 10-30° C. during 10-45 min and exposing the plurality of cells to at least one magnetic particle under conditions effective to allow the direct or indirect coupling of the magnetic particle to the specific marker CD52 expressed on the surface of the spermatozoa,
iii) recovering the plurality of cells and
iv) separating the spermatozoa that are coupled to the magnetic particle from the cells not coupled to the magnetic particle.
Step i)

Surprisingly, the Applicants have shown that the presence of serum within the buffer used during the cell recovery process results in non-specific antibodies binding during the staining process performed post cell recovery. Accordingly, the plurality of cells contained on an inert substrate is obtained by contacting said inert substrate with a serum-free buffer.

Most preferably, the plurality of cells are contacted with serum-free buffer comprising Phosphate buffered saline 1× and about 2-20 mM of EDTA, at about 10-30° C. during 10-45 min. Even more preferably, the serum-free buffer comprises about 2-10 mM of EDTA and the plurality of cells is contacted with said serum-free buffer at 25° C. during 30 min.

Preferably also, the serum-free buffer further comprises about 10-200 ng/ml of proteinase K most preferably, about 10-100 ng/ml, even more preferably about 10 ng/ml. The Applicants have surprisingly shown that, the addition of proteinase K to the serum-free buffer greatly enhances the number of spermatozoa recovered by this technique.

Figure 11:
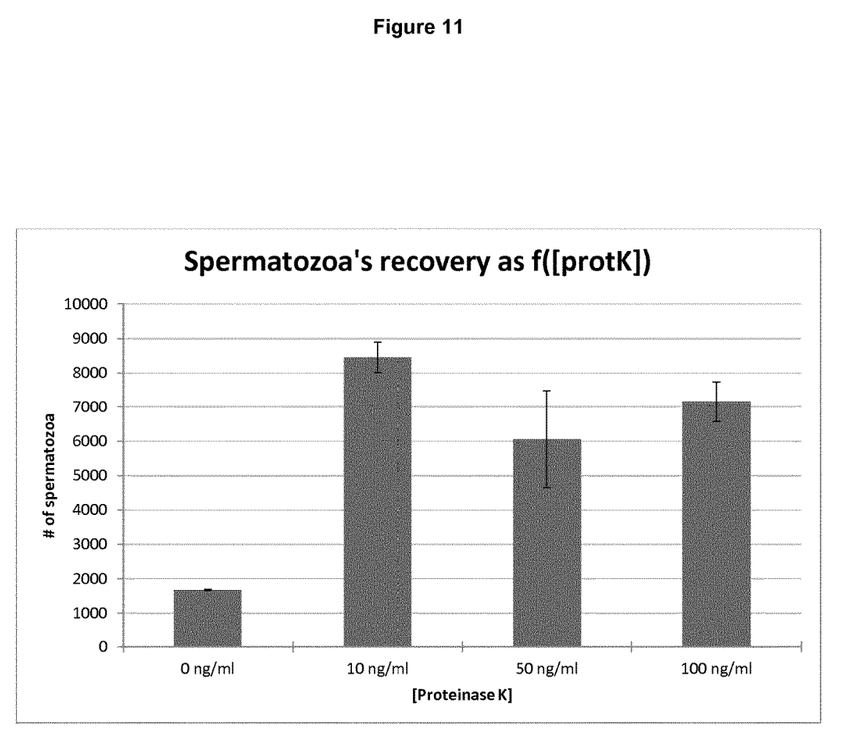
FIG. 11. Swabs were loaded with 20 µl of 125×PBS-diluted sperm. Swabs were left to dry for two days. Spermatozoa were recovered from swabs, as described in Example 1, in PBS 2 mM EDTA with increasing concentration of proteinase K. Number of recovered spermatozoa was evaluated through FACS counting post-recovery.

As can be deducted from FIG. 11 (Example 3), increasing the concentration of proteinase K in the serum-free buffer increases the number of recovered spermatozoa as evaluated through FACS counting post-recovery.

Without wishing to be bound by the theory, a possible explanation would be that the cells of interest are kept intact and thus do not clog the columns during the separation step. For example, most of the epithelial cells are not kept intact after the recovery step in presence of the proteinase K. The spermatozoa on the other hand are still intact and thus can be separated from epithelial cells (both intact and debris) in the columns. Counted epithelial cells post recovery in presence of Proteinase K decrease significantly compared to recovery in absence of proteinase K. The DNA profile of the epithelial cells donor can still be obtained using the supernatant of the recovery buffer post centrifugation. The flow through of the column (non-spermatic fraction) can still results in the DNA profile of the epithelial cells donor, but most of the material originating from these cells is in the supernatant post-recovery; as epithelial cells are partially lysed, the risk of clogging the column with those large cells decreases)

The plurality of cells are selected from the non-limiting group comprising spermatozoa, epithelial cells, vaginal cells, buccal epithelial cells, white blood cells and red blood cells. The plurality of cells is usually in a dry state form.

The inert substrate of the invention can be any substrate that has been contacted, intentionally or unintentionally, with the plurality of cells of the invention. The inert substrate can be selected from the non-limiting group comprising underwear, outfit, tissue, cloth, swab, hair, clothing, plastic items, leather items (jacket, trousers, ... ), bed sheets, towels and condoms.

The plurality of cells is then recovered, e.g., by sedimentation, i.e. by applying centrifugal forces during, for example, 5 minutes at 300 g, and supernatant is removed (or kept as it contains most of the non-spermatozoa cells' DNA, ie the epithelial cells DNA). The cell pellet contains the plurality of cells as well as cell debris.

Alternatively or additionally, the method further comprises a step of washing the plurality of cells contacted with the serum-free buffer with a washing buffer. Generally, the washing buffer consists in Phosphate buffered saline 1× and about 2-20 mM EDTA at a temperature at about 4° C. to 25° C.

Step ii):

The plurality of cells obtained in step i) and contained in the cell pellet is then contacted with a buffer and exposed to at least one magnetic particle under conditions effective to allow the direct or indirect coupling of the magnetic particle to the specific marker expressed CD52 expressed on the surface of the spermatozoa.

In the case of direct coupling, the conditions effective to allow the direct coupling of the magnetic particle to the specific marker CD52 expressed on the surface of the spermatozoa comprise the step of contacting the plurality of cells obtained from said inert substrate with a buffer comprising Phosphate buffered saline (PBS) 1× and about 2-20 mM EDTA 2 mM during 5 to 30 minutes at a temperature comprised between about 4° C. to 25° C. and containing at least one magnetic particle labeled with a binding partner that specifically binds to the marker CD52 expressed on the surface of spermatozoa, optionally under agitation.

Preferably, the binding partner that specifically binds to the marker CD52 expressed on the surface of the spermatozoa is conjugated with a label moiety. Most preferably, the binding partner is an antibody or an antigen-binding portion thereof.

In the case of indirect coupling, the conditions effective to allow the indirect coupling of the magnetic particle to the specific marker CD52 expressed on the surface of spermatozoa comprise the steps of i) first contacting the plurality of cells obtained from said inert substrate with a serum-free buffer comprising Phosphate buffered saline (PBS) 1× and about 2-20 mM EDTA further containing a binding partner to the specific CD52 marker during 5 to 30 minutes at a temperature comprised between 4° C. to 25° C., optionally under agitation, thereby labeling the cells of interest with said binding partner, wherein said binding partner is biotinylated, unconjugated or conjugated with a label moiety, ii) contacting the plurality of cells of step i) containing the spermatozoa coupled with the binding partner, with a magnetic particle comprising a molecule specifically recognizing the binding partner, the biotin or the label moiety conjugated to said binding partner.

Usually, the binding partner that specifically binds to the marker CD52 expressed on the surface of the spermatozoa is an antibody or an antigen-binding portion thereof.

In both cases (indirect and direct couplings), the EDTA concentration in the serum-free buffer is from about 2-10 mM, most preferably about 2 mM.

As used throughout the description, the term "antibody" is intended to include polyclonal and monoclonal antibodies, chimeric antibodies, bispecific antibodies, haptens and antibody fragments, and molecules which are antibody equivalents in that they specifically bind to an epitope on the product antigen. The term "antibody" includes polyclonal and monoclonal antibodies of any isotype (IgA, IgG, IgE, IgD, IgM), or an antigen-binding portion thereof, including, but not limited to, F(ab) and Fv fragments such as sc Fv, single chain antibodies, chimeric antibodies, humanized antibodies, recombinant engineered antibody (such as REAfinity™ Antibodies, Myltenyi Biotec GmbH) and a Fab expression library. The "Bispecific antibody" antibodies can also be immobilized for instance on a polymer or a particle.

An "an antigen-binding portion" of the amino acid sequence of an antibody of the invention refers to a sequence containing less amino acids in length than the corresponding sequence. This antigen-binding portion can be used as long as it exhibits the same properties as the sequence from which it derives Preferably this antigen-binding portion contains less than 90%, preferably less than 60%, in particular less than 30% amino acids in length than the respective antibody sequence.

As used herein, a "label moiety" is detectable, either directly or indirectly. The label moiety can be detectable label. Direct label moieties include radioisotopes; enzymes whose products are detectable (e.g., luciferase, β-galactosidase, and the like); fluorescent labels (e.g., fluorescein isothiocyanate (FITC), rhodamine, phycoerythrin, a cyanine dye, Cascade Blue, PerCP, Cy5, Cy7, allophycocyanin (APC), PECy5 or other tandem conjugates of different fluorochromes, Texas Red, and the like); fluorescence emitting metals, e.g., 152Eu, or others of the lanthanide series, attached to the protein through metal chelating groups such as EDTA; chemiluminescent compounds, e.g., luminol, isoluminol, acridinium salts, and the like; bioluminescent compounds, e.g., luciferin, aequorin (green fluorescent protein), and the like; and metallic compounds. Indirect label moieties include labeled molecules that bind to the polypeptide, e.g., antibodies specific for the polypeptide, wherein the labeled binding molecule is labeled as described above; and members of specific binding pairs, e.g., biotin, (a member of the specific binding pair biotin-avidin), digoxigenin (a member of the specific binding pair digoxigenin-antibody to digoxigenin) and the like. Alternatively the label moiety can be any suitable label including but not limited to those described herein.

Some methods for cell sorting utilize magnetic separations, and some of these methods utilize magnetic particles or beads. Different magnetic particles are available from a number of sources, including for example, Dynal (Norway), Advanced Magnetics (Cambridge, Mass., U.S.A.), Immuncon (Philadelphia, U.S.A.), Immunotec (Marseilles, France), and Miltenyi Biotec GmbH (Germany). Preferred magnetic labeling methods include colloidal superpara magnetic particles in a size range of 5 to 200 nm, preferably in a size of 10 to 100 nm. These magnetic particles allow a quantitative magnetic labeling of cells, thus the amount of coupled magnetic label is proportional to the amount of bound product, and the magnetic separation methods are sensitive to different amounts of product secretion. Colloidal particles with various specificities are known in the art, and are available, for example, through Miltenyi Biotec GmbH.

Magnetic particles labeled with a binding partner such as an antibody, a protein, or a nucleic acid molecule are commercially available from Miltenyi Biotec GmbH (Friedrich Ebert Str. 68, D-51429 Bergisch Gladbach, Germany). Methods for magnetically labeling a biomolecule are known in the art; any known method can be used. For example, U.S. Pat. No. 6,020,210 describes methods for preparation of magnetic particles, and attachment of biomolecules thereto. A first member of a specific binding pair can be associated with a magnetic particle, wherein the biomolecule to be modified comprises a moiety that binds to the member of the specific binding pair. Alternatively, the magnetic particle is coupled, e.g. to the antibody or the immunologically reactive fragment thereof, through a linker or a spacer (such as, e.g., a nucleic acid linker). Addition of spacers or linkers will allow biomolecules to be presented in a more flexible fashion, and careful chemistry can attach ligands in a specific orientation. There are numerous chemistries used for these couplings as many companies have published protocols and will help the artisan skilled in the art with the chemistry.

Examples of members of specific binding pairs that can be attached to a magnetic particle include, but are not limited to, oligo dT (for binding to nucleic acid molecules comprising, e.g., a poly-A tract at the 3' end); oligonucleotides having a specific nucleotide sequence (for binding to nucleic acid molecules comprising a complementary nucleotide sequence); avidin (e.g., streptavidin) (for binding to a biotinylated biomolecule); an antigen-binding polypeptide, e.g., an immunoglobulin (Ig) or epitope-binding fragment thereof (for binding to a biomolecule comprising an epitope recognized by the Ig); polynucleotide binding proteins (for binding to a polynucleotide), e.g., a transcription factor, a translation factor, and the like; Ni or Co chelate (to immobilize poly-histidine-tagged proteins); receptor-ligand systems, or other specific protein-protein interacting pairs; aptamers (e.g., nucleic acid ligands for three-dimensional molecular targets); lectins (for binding glycoproteins); lipids and phospholipids (binding to lipid-binding proteins), e.g., phosphatidyl serine and annexin V. Those skilled in the art will recognize other members of specific binding pairs that may be attached to a magnetic particle.

A biomolecule can also be coupled (covalently or non-covalently) to a magnetic particle by direct chemical conjugation or by physical association. Such methods are well known in the art. Biochemical conjugations are described in, e.g., "Bioconjugate Techniques" Greg T. Hermanson, Academic Press. Non-covalent interactions, such as ionic bonds, hydrophobic interactions, hydrogen bonds, and/or van der Waals attractions can also be used to couple a biomolecule with a magnetic particle. For example, standard non-covalent interactions used to bind biomolecules to chromatographic matrices can be used. One non-limiting example of such a non-covalent interaction that can be used to bind a biomolecule to a magnetic particle are DNA binding to silica in the presence of chaotropic salts. Those skilled in the art are aware of other such non-covalent binding and conditions for achieving same. See, e.g., Molecular Cloning, Sambrook and Russell, Cold Spring Harbor Laboratory Press.

Step iii)

Prior to separating the cells, the cells are preferably washed, recovered by, e.g. sedimentation techniques while supernatant is removed.

Washing may serve to remove unbound components. Such washing steps may serve various functions, including: removal of modifying components of the modification reaction; removal of unwanted by-products of the modification reaction; stopping a particular modification reaction; exchanging a buffer; desalting; removal of nucleic acid fragments; removal of enzymes; removal of cofactors; removal of proteins; removal of non-specifically bound molecules; changing the pH; and stabilization of an intermediate.

The composition and temperature of a washing solution may vary according to the desired result. The optimal composition and temperature of a washing solution can readily be determined by those skilled in the art.

Wash solutions may comprise a buffer, and may further comprise additional components, as necessary, including, but not limited to, a chelating agent, e.g, EGTA, EDTA; a detergent, e.g, sodium dodecyl sulfate, Triton X-100; CHAPS, etc.; various ions; reducing agents (e.g, DTT, DTE, β-mercaptoethanol, and cysteine); salts; glycerol; tRNA; nuclease inhibitors; protease inhibitors; cofactors; polyamines; nucleotides; nucleotide analogs; glycogen; albumin; imidazole; denaturing agents (e.g, urea, guanidinium chloride, and the like); peptides (e.g, glutathione); etc.

Step iv)

The cells that are coupled to the magnetic particle from those not coupled to the magnetic particle are then separated by any suitable magnetic separation methodology known in the art. Preferably, the cells are applied to a column within a separation device such as MACS® Columns (Miltenyi Biotec GmbH) and separation is conducted in a source of magnetic field.

Alternatively or additionally, the magnetic separation can be accomplished with high efficiency by combining a second force to the attractive magnetic force, causing a separation based upon the different strengths of the two opposed forces. Typical opposed forces are, for example, forces induced by magnetic fluids mixed in the separation medium in the magnetic separation chamber, gravity, and viscous forces induced by flow speed of medium relative to the cell. Any magnetic separation method, preferably magnetic separation methods allowing quantitative separation will be used. It is also contemplated that different separation methods can be combined, for example, magnetic cell sorting can be combined with FACS, to increase the separation quality or to allow sorting by multiple parameters.

Preferred techniques include high gradient magnetic separation (HGMS), a procedure for selectively retaining magnetic materials in a chamber or column disposed in a magnetic field. In one application of this technique the product is labeled by attaching it to a magnetic particle. The attachment is generally through association of the product with a label moiety which is conjugated to a coating on the magnetic particle which provides a functional group for the conjugation. The captured product thus coupled to a magnetic "label", is suspended in a fluid which is then applied to the chamber. In the presence of a magnetic gradient supplied across the chamber, the magnetically labeled target cell is retained in the chamber; if the chamber contains a matrix, it becomes associated with the matrix. Cells which do not have or have only a low amount of magnetic labels pass through the chamber.

The wash step performed while the spermatozoa are still in the column, and the column is still in the magnet also helps to remove potential cell-free DNA originating from the non-spermatozoa fractions of the original cell-mixture. This will be especially useful in cases where the original plurality of cells consists of very few spermatozoa among large amount of epithelial cells. Cell free DNA originating from the epithelial cells has to be removed as much as possible from the spermatozoa, in order not to interfere with the spermatozoa's DNA when obtaining a DNA profile post-separation.

The retained cells can then be eluted by changing the strength of, or by eliminating, the magnetic field or by introducing a magnetic fluid or by flushing the retained cells out of the column with PBS 2 mM EDTA, once removed from the magnet. The selectivity for a captured product is supplied by the label moiety conjugated either directly or indirectly to the magnetic particle or by using a primary antibody and a magnetic particle recognizing the primary antibody. The chamber across which the magnetic field is applied is often provided with a matrix of a material of suitable magnetic susceptibility to induce a high magnetic field gradient locally in the chamber in volumes close to the surface of the matrix. This permits the retention of fairly weakly magnetized particles. Publications describing a variety of HGMS systems are known in the art, and include, for example, U.S. Pat. No. 4,452,773, U.S. Pat. No. 4,230,685, PCT application WO85/04330, U.S. Pat. No. 4,770,183, and PCT/EP89/01602; systems are also described in U.S. Pat. Nos. 5,411,863; 5,543,289; 5,385,707; and 5,693,539, which are commonly owned and hereby incorporated herein by reference.

Other embodiments can also include analyzing the cell population to detect labeled cells, if any, and if desired, sorting the labeled cells, if any.

The immobilized biomolecule or other component may be eluted from the separation device after a modification procedure(s). In some embodiments, the immobilized biomolecule is retained on the column, and only a product of a modification reaction is eluted. In other embodiments, both the immobilized biomolecule and a product of a modification reaction (where the product of the modification reaction is other than the immobilized biomolecule) are eluted. In still other embodiments, where the immobilized biomolecule is modified by a modification reaction, only the modified immobilized biomolecule is eluted. The biomolecule to be immobilized can contain, or can be modified to contain, a site for proteolytic cleavage, or a site for cleavage by a restriction endonuclease, such that, when desired, e.g., after one or more modification steps, the modified immobilized biomolecule can be contacted with an appropriate enzyme (e.g, a proteolytic enzyme that specifically acts on the proteolytic cleavage site; a restriction endonuclease that acts on the restriction endonuclease recognition site), and the modified immobilized biomolecule can be released from the column. The biomolecule can be eluted together with the magnetic particle or separately from the magnetic particle, e.g, the magnetic particle is retained on the column, while the biomolecule is released from the magnetic particle.

Preferably, in the method of the present invention steps i) and ii) can be repeated several times where necessary.

The methods of the invention may be used for positive cell selection or negative cell selection. In positive cell selection, cells of interest, i.e. spermatozoa, are bound and removed from a sample. In contrast, in negative cell selection contaminating cells, such as dying or dead cells or indeed components from dying or dead cells, are removed from a sample.

The term "labeled" as used in the present invention means that a molecule, e.g. an antibody, is conjugated to a label. Many different labels that can be conjugated to an antibody are known to the skilled artisan. For example, radioisotopes, e.g., $^{32}$P, $^{35}$S or $^{3}$H; fluorescence or luminescence markers, e.g. fluorescein (FITC), rhodamine, TEXAS RED, phycoerythrin (PE), allophycocyanin (APC), 6-carboxyfluorescein (6-FAM), 2',7'-dimethoxy-4',5'-dichloro-6-carboxyfluorescein (JOE), 6-carboxy-X-rhodamine (ROX), 6-carboxy-2',4',7',4,7-hexachlorofluorescein (HEX), 5-carboxyfluorescein (5-FAM) or N,N,N',N'-tetramethyl-6-carboxyrhodamine (TAMRA); antibodies or antibody fragments, e.g. F(ab)2 fragment; affinity labels, e.g. biotin, avidin, agarose, bone morphogenetic protein (BMP), matrix bound, haptens; and enzymes or enzyme substrates, e.g. alkaline phosphatase (AP) and horseradish peroxidase (HRP).

Preferably, the cells of the plurality of cells contained on an inert substrate are selected from the group comprising spermatozoa and epithelial cells. Most preferably, the cells of interest are spermatozoa.

In case the cells of interest are spermatozoa, the specific marker expressed on the surface of the spermatozoa is, e.g. the Human epididymal secreted protein CD52. CD52 is a glycosylphosphatidylinositol (GPI)-anchored heavily glycosylated antigen. It is absent from immature spermatozoa within testis or in the efferent ducts. CD52 is secreted in the seminal plasma by the epididymis and is inserted in the spermatozoa membrane via GPI-anchor as the spermatozoa pass through the epididymis. CD52 is found almost predominantly on the spermatozoa's head, whereas the tail is substantially devoid of it (ref. C. Kirchhoff, Mol Hum Rep (1996) Vol 2. No 1: 9-17)

The methods of the invention can be used to increase purity of aggressor cells in all possible combination as long as it contains sperm cells, and can also enable identification of the perpetuator in male-male sexual aggression (something difficult to achieve using Y-STR).

Advantages of this method over other approaches (i.e. laser dissection, fluorescence activated cell sorting, differential lysis) is the absence of expensive technologies (laser dissection, cell sorting), no need for a skilled operator, absence of detergent during the separation of the samples thus preventing loss of material in compromised samples due to unwanted DNA lysis, staining and separation is done in 30-40 minutes, major and minor contributor profiles can be obtained, automation is possible to reduce backlogs, low contamination risk as separations are done in single use individual columns, little wash-step and medium exchange required and application of the very same technology for separation of other type of samples, as long as specific antibodies are available for discrimination.

Preliminary analysis using flow cytometry acquisition and analysis showed that it was possible to recover approximately 40% of the input sperm number on dried 3 days old swabs after a simple and fast recovery procedure and a very simple 3 colors staining approach.

The MACS method has the advantage over the differential lysis protocol to avoid using detergent, which can potentially harm already partially degraded DNA material within the cells. The population of interest enrichment is done through surface selection of a given set of markers presents on only one subset of cells and absent from the other All experimental steps are done within PBS, an isotonic solution, which will lower risks of affecting the cells integrity more than it may already be on several days, weeks, or months old samples.

The selection is therefore done with biological specificity to a surface protein identification profile, different for each cell type.

Moreover, a simple DNA content control can be performed in case of epithelial cells mixed with sperm cells, as epithelial cells contain 2n DNA whereas sperm only contain n DNA. Labeling DNA with a fluorescent probe (i.e. Propidium iodid (PI)) will give a signal intensity proportional to the DNA content, resulting in two PI peaks, one high for epithelial cells and one low for sperm cells. Simple control containing only one type of cells (EC or SP) can be prepared in parallel to ensure the PI expression level for each cell type.

The present invention also concerns a method for selectively enriching cells in spermatozoa according to the specific marker CD52 (Human epididymal secreted protein) expressed on their surface from a plurality of cells contained, in a dry state, on an inert substrate, which method comprises the steps of
  i) obtaining the plurality of cells contained on the inert substrate,
  ii) contacting said plurality of cells with a serum-free buffer comprising Phosphate buffered saline 1× and about 2-20 mM of EDTA, at about 10-30° C. during 10-45 min and exposing the plurality of cells to at least one magnetic particle under conditions effective to allow the direct or indirect coupling of the magnetic particle to the specific marker CD52 expressed on the surface of the spermatozoa,
  iii) recovering the plurality of cells and
  iv) separating the spermatozoa that are coupled to the magnetic particle from the cells not coupled to the magnetic particle.

Additionally, the present invention also envisions a kit for practicing one or more of the above-described methods. Preferably, said kit comprising one or more reagents, one or more magnetic particle, one or more binding partner and/or instructions for use.

Reagents of interest include reagents useful for preparing the buffers of the invention. The kit may further comprise a column comprising a matrix composed of ferromagnetic spheres.

In addition to the above components, the kits will further include instructions for practicing the methods described herein. These instructions may be present in the kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another means would be a computer readable medium, e.g., diskette, CD, etc., on which the information has been recorded. Yet another means that may be present is a website address which may be used via the internet to access the information at a removed site. Any convenient means may be present in the kits.

The one or more binding partner comprised in the kit of the invention is usually biotinylated, unconjugated or conjugated with a label moiety.

The one or more magnetic particle of comprises a molecule specifically recognizing the binding partner, the biotin or the label moiety conjugated to said binding partner.

Preferably, the molecule specifically recognizing the binding partner, the biotin or the label moiety conjugated to said binding partner is an antibody or an antigen-binding portion thereof.

The present invention also comprises a magnetic particle labeled with a binding partner that specifically binds to a marker CD52 expressed on the surface of the spermatozoa. Usually, said binding partner is biotinylated, unconjugated or conjugated with a label moiety and is an antibody or an antigen-binding portion thereof. The magnetic particle of the invention, in a size range of 5 to 200 nm, preferably in a size of 10 to 100 nm, is preferably coupled to the antibody or the antigen-binding portion thereof through a linker.

Another object concerns the use of a kit of the present invention for i) for selectively enriching cells in spermatozoa or for ii) separating spermatozoa according to the specific marker CD52 (Human epididymal secreted protein) expressed on their surface from a plurality of cells, wherein said kit comprises one or more reagents, one or more magnetic particles, one or more binding partner and/or instructions for use.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

EXAMPLES

Example 1

Material and Methods
Samples Preparation

Samples can be gynecological swabs, sperm stains on clothes, microscope slides used for spermatozoa morphological identification. Mock samples were prepared by rubbing swabs on the inner cheek of female donors and loading them with 20 µl of sperm with increasing dilutions, down to approximately 500 spermatozoa per swab. Once loaded with both cells types, swabs were left to dry at RT° C. for two hours before being returned in their protective cases and stored at RT° C. in the dark.

Cells Recovery from Swabs

Swabs were cut open in half with a clean razor blade before the external layer of cotton (where the cells are found) was transferred into a 1.5 ml Eppendorf briefly vortexed and incubated in 800 µl PBS+2 mM EDTA at 25° C. for 30 minutes on a thermomixer at 700 rpm. To increase cell number recovery, the Eppendorf could be briefly vortexed again after the 30 minutes incubation and the cotton swab-head could be agitated with tweezers in the Eppendorf. The shred cotton head was then placed in a spin basket, washed once with 150 µl PBS+2 mM EDTA, and centrifuged for 5 minutes at 300 g. Both liquid fractions, 800 ul from the initial recovery step and 150 µl from the wash step, were pooled together and centrifuged again for 10 minutes at 300 g. Supernatant was removed and the cell pellet (containing spermatozoa and epithelial cells) was stained.

Samples Staining

Each cell pellet was resuspended in 50 µl PBS+2 mM EDTA+4 µl anti-CD52 FITC (clone REA164, Miltenyibiotec, Bergisch Gladbach, Germany) and stained for 10 minutes at 4° C. in the dark. Cells were then washed twice with 150 ul PBS+2 mM EDTA and centrifuged for 10 minutes at 300 g. Supernatant was removed and the cell pellet was resuspended in 50 µl PBS+2 mM EDTA+10 µl anti-FITC microbeads (Miltenyibiotec, Bergisch Gladbach, Germany) and stained for 15 minutes at 4° C. in the dark. Cells were washed twice with 150 µl PBS+2 mM EDTA and centrifuged at 300 g. Cell pellet was then resuspended in 300 µl PBS+2 mM EDTA and kept at 4° C. until MACS separation.

MACS Separation

MACS LC column (Miltenyibiotec, Bergisch Gladbach, Germany) were prepared by rinsing twice with 500 ul PBS+2 mM EDTA at 4° C. The stained cell suspension was then added in the column and the epithelial cell containing flow-through was collected in an Eppendorf. The column was washed twice with 500 µl PBS+2 mM EDTA. The column was then removed from the magnet and placed into a new clean 1.5 ml Eppendorf. 800 µl PBS+2 mM EDTA was added into the column and the spermatozoa were flushed out of the column by applying pressure onto the plunger. Both the sperm containing positive fraction and the epithelial cells containing flow-through were further processed to lyse the two separated cell types independently from one another.

FACS Analyses

CD52 expression on sperm cells and absence of expression on epithelial cells was monitored by flow cytometry analysis (FACSCanto, Becton Dickinson, N.J., USA) on fresh samples as well as samples recovered from dry state using anti-CD52 FITC antibody (clone REA164, Miltenyibiotec). The specificity of the CD52 staining to the spermatozoa and the absence of surface marker exchange between both cell types during samples preparation, storage and recovery was also tested and confirmed. Separation efficiency was evaluated by flow cytometry (LSR II, Becton Dickinson, N.J., USA) adding 5 µl of propidium iodide (Life Technologies) to the samples prior to acquisition. Based on morphological parameters (forward and side scatters) and fluorescence (CD52 FITC, PI) sperm cells (low forward scatter, low side scatter, CD52 positive, haploid PI signal) can be differentiated from epithelial cells (high forward scatter, high side scatter, CD52 negative and diploid PI signal).

Cell Lysis and DNA Extraction

DNA from both spermatic fraction and epithelial cells fraction was obtained using the QiaAmp kit from Qiagen following the provided protocol. Briefly, the cell pellet was resuspended in 200 µl PBS, 200 µl of AL buffer and 20 µl of proteinase K are added. For the spermatic fraction 1.5 mg DTT in 10 ul H20 was added to the lysis buffer. Eppendorfs were vortexed for 15 minutes and then incubated for 45 minutes at 56° C. under mild agitation. After a brief centrifugation, 200 µl of pure ethanol was added and the samples were vortexed and briefly centrifugated. The liquid fraction was transferred on a QiaAmp spin column and centrifuged 1 minute at 8000 rpm. Collection tube was changed and 500 µl of AW1 solution was added to the column. Another one minute centrifugation at 8000 rpm was performed before another collection tube was used and 500 µl of AW2 solution were added in the column. The column was centrifuged for 3 minutes at 14'000 rpm, the flow-through was discarded and the column was centrifuged again for 1 minute at 14'000 rpm. Finally the column was placed onto a new sterile 1.5 ml Eppendorf, 70 µl of AE buffer was added and the column was centrifuged for 1 minute at 8000 rpm after one minute incubation at RT° C.

DNA Quantification, NGM Select Amplification and Profiles Analyses

DNA content of all the fractions was quantified using the Human and Y DNA quantifiler kit (Life Technologies) and STR profile was obtained with AmpFLSTR NGM Select kit (Life technologies) according to the manufacturer protocol. Electropherograms were obtained by running AmpFLSTR NGM Select amplification product on a 3130 xl Genetic Analyzer from Applied Biosystems. STR profiles were analyzed with Applied Biosystems' Gene Mapper V 3.2.1.

Example 2

Results

CD52 Cell Staining is Sperm Specific

In order to be used for MACS cell separation, the staining used must imperatively be specific to the cell type that one want to keep in the positive fraction, and not to other cell types present in the original sample.

Figure 1:
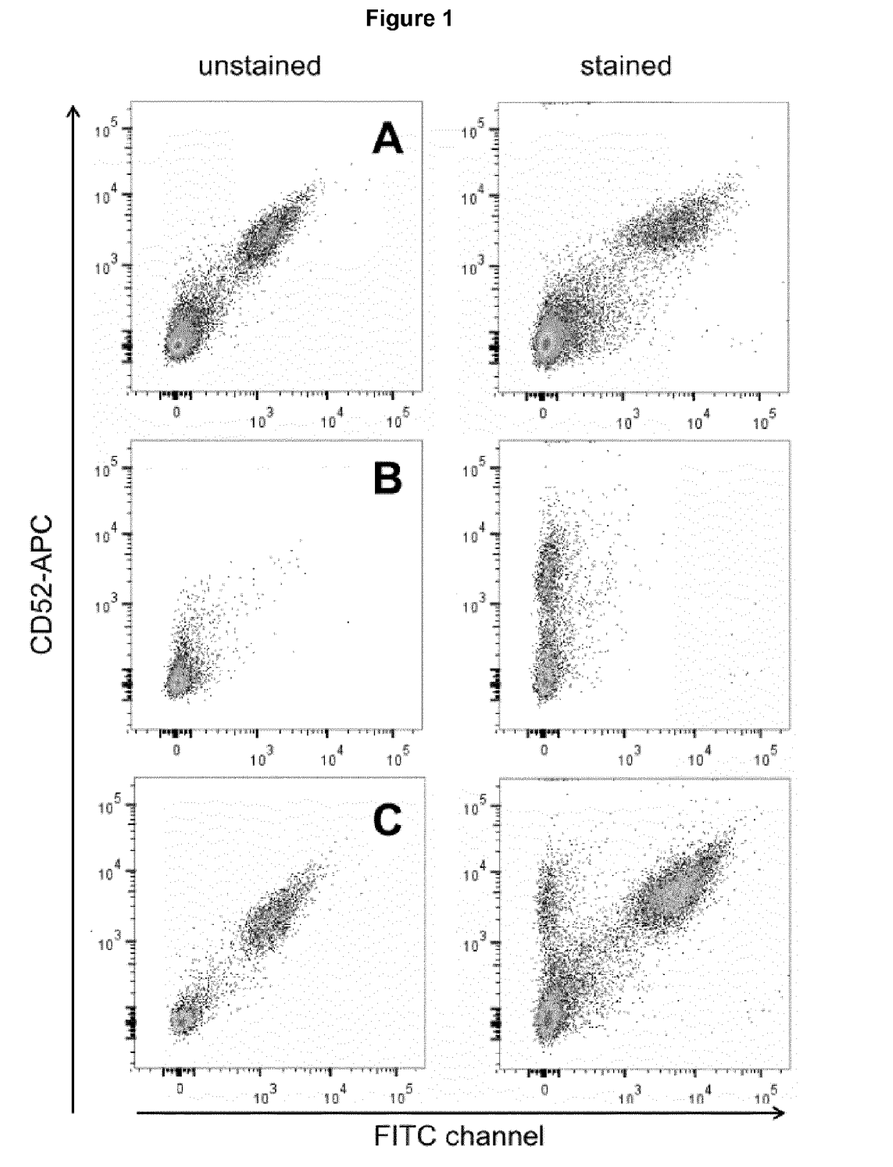
FIG. 1. CD52-APC expression on fresh samples. (A) Epithelial cells only. (B) Spermatozoa only. (C) Mix of epithelial cells and spermatozoa. A strong spermatozoa-specific shift is observed for spermatozoa once stained with CD52 (B), whereas only a slight shift is observed for epithelial cells (A).

Samples composed of mixes of fresh epithelial cells obtained from smear from the lining of the mouth and serially diluted liquefied sperm were stained with CD52 and propidium iodide prior to flow cytometry analyses (FIG. 1).

CD52 Specificity is Kept Post Recovery of Dry Sample

Figure 2:
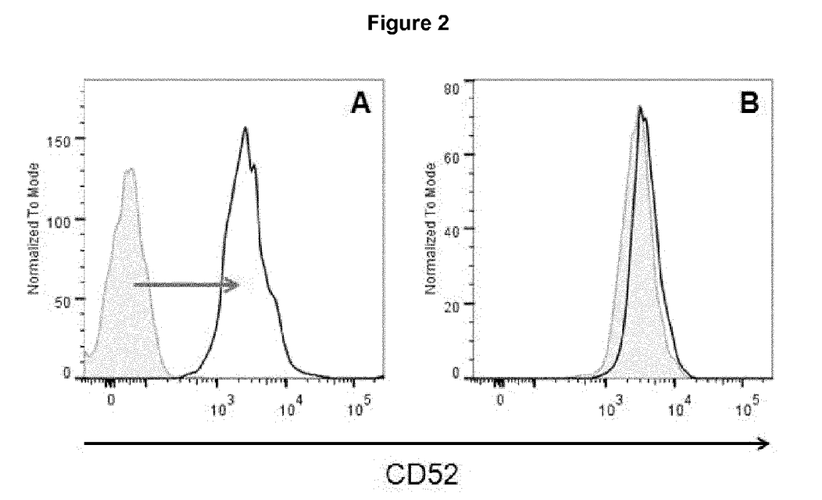
FIG. 2. Specific CD52 expression on the surface of spermatozoa and epithelial cells recovered from dry state. Recovered spermatozoa (A) show a strong shift in fluorescence once stained with CD52 compared to unstained autofluorescence (grey curve), whereas no shift is observed for the epithelial cells (B) when compared to unstained autofluorescence (grey curve).

As samples are stored on swabs in a dry state, one must ensure that the staining specificity remains after the cells recovery from the swabs to achieve efficient separations. Mixes of epithelial cells and spermatozoa were prepared and seeded onto swabs. Once dried, the swabs were returned in their protective case and stored at RT° C. from several days up to two months, before the cells were recovered, stained and analyzed by flow cytometry. CD52 staining remained specific to the spermatozoa with a strong shift in fluorescence, whereas a very low shift to higher fluorescence was measured for epithelial cells (FIG. 2).

This indicated that not only the specificity of CD52 can still be used to discriminate spermatozoa from epithelial cells, even post-recovery, but also that no transfer of CD52 occurred between spermatozoa and epithelial cells during the samples preparation procedure, storage and recovery.

Figure 3:
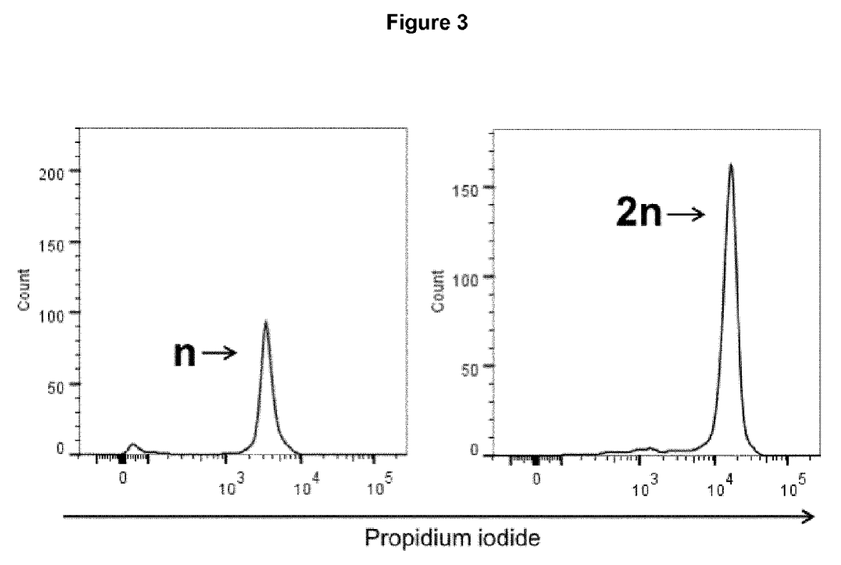
FIG. 3. Propidium iodide fluorescence intensity comparison between spermatozoa and epithelial cells. Haploid (n) spermatozoa (left) stained with propidium iodide result in a lower fluorescent signal than diploid (2n) epithelial cells (right).

Spermatozoa can also be differentiated from epithelial cells by flow cytometry. Staining with DNA stain propidium iodide will result in a signal intensity proportional to the amount of DNA found within the cell. Therefore, diploid epithelial cells will result in a stronger signal that haploid spermatozoa (FIG. 3).

Figure 4:
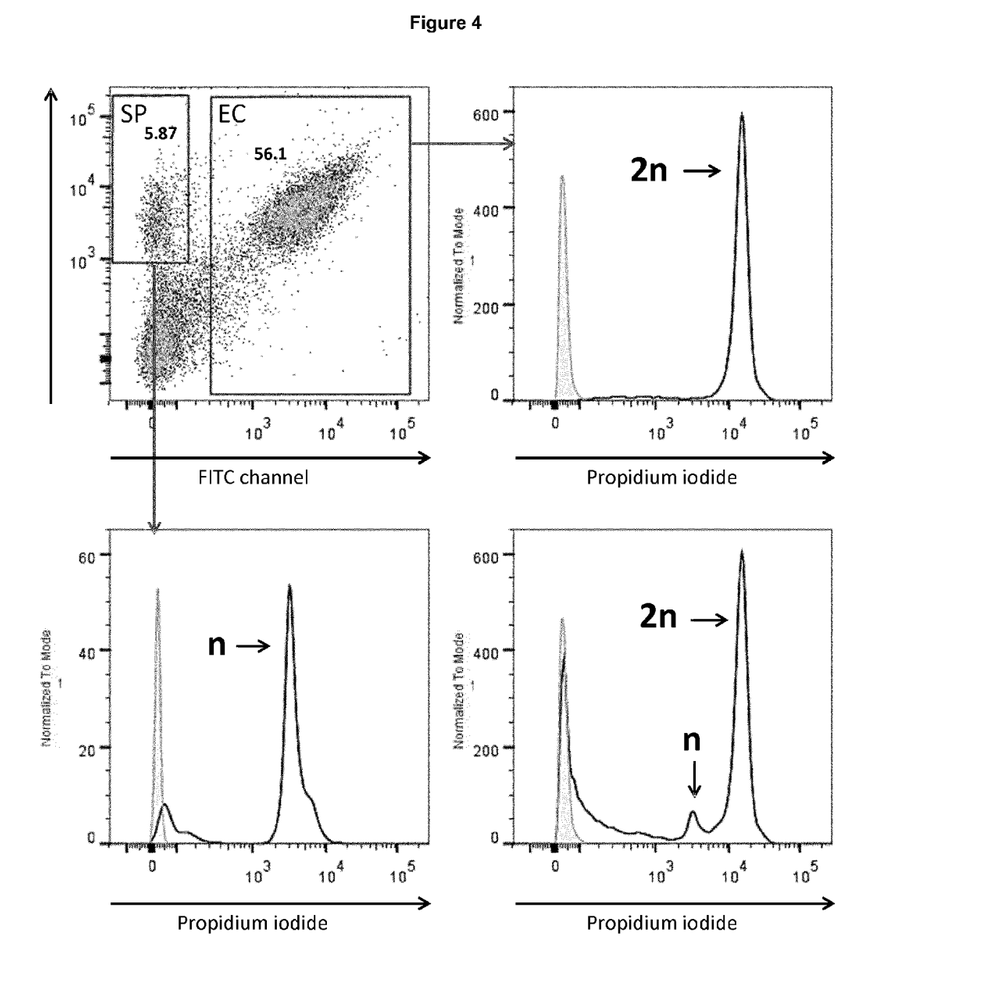
FIG. 4. CD52 positive events in mixed spermatozoa-epithelial cells present a haploid propidium iodide fluorescence profile. Gating spermatozoa (SP) and epithelial cells (EC) regions of interest on a stained mixed sample (upper left) showed haploid profile for CD52 positive spermatozoa (lower left) and diploid profile for CD52 negative epithelial cells (upper right). Grey curve represents unstained mixed samples. Ungated whole mixed spermatozoa and epithelial cells sample (lower right) shows both haploid and diploid propidium iodide peaks as well as propidium iodide negative events.

Using this property, CD52 specificity for spermatozoa could be further checked by gating region of interest on recovered mixed spermatozoa-epithelial cells samples stained with both CD52 and propidium iodide (FIG. 4).

The propidium iodide negative events observed within the CD52 positive gate for spermatozoa (FIG. 4) may reflect the presence of CD52 positive DNA-free particles such as spermatozoa tails, or spermatozoa debris.

MACS Separation Provides Sperm Only Positive Fraction

Figure 5:
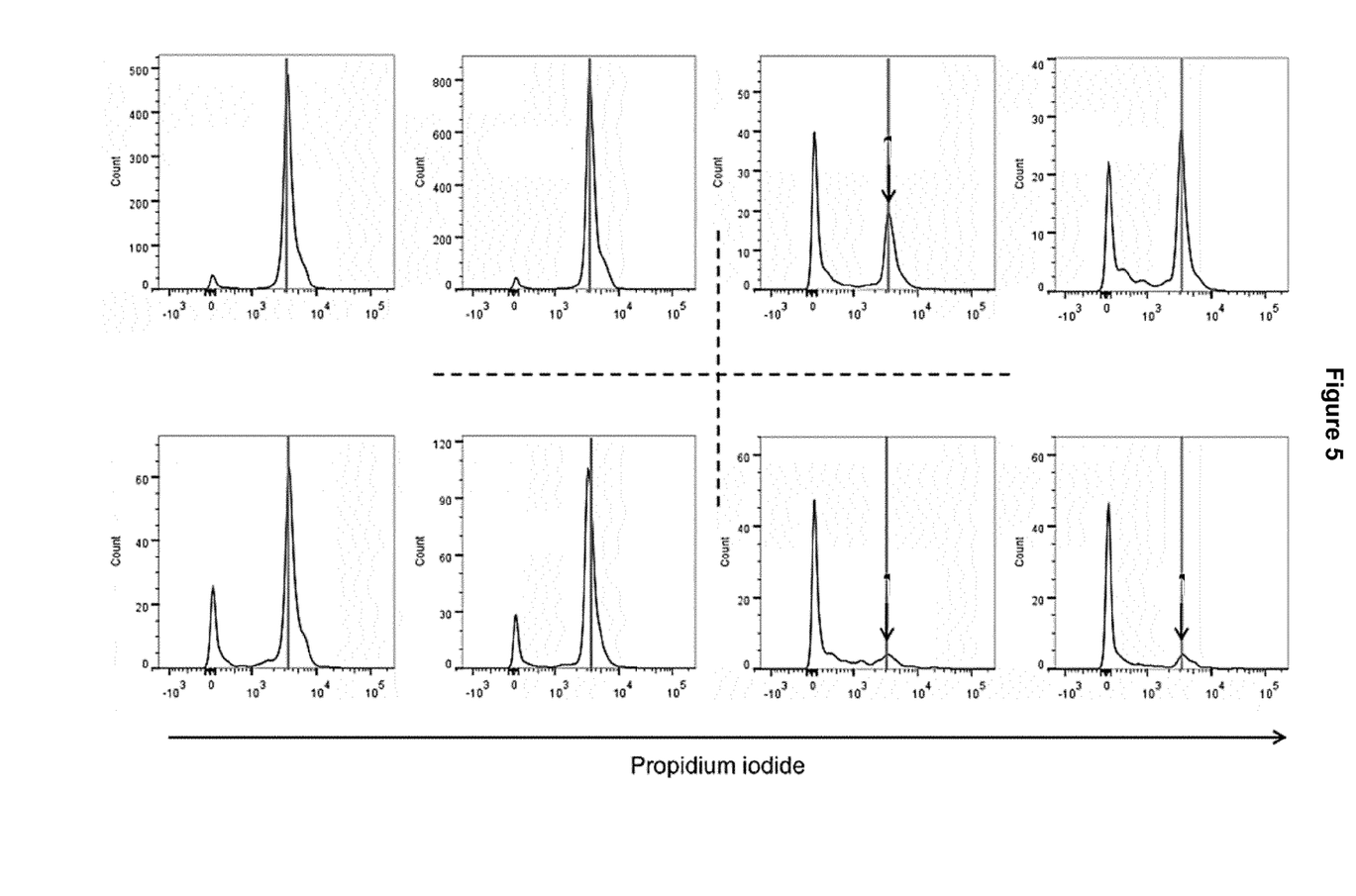
FIG. 5. Propidium iodide staining of the positive fractions post-MACS separation. Different amount of spermatozoa were seeded onto swabs loaded with 1e+6 epithelial cells. Positive fractions obtained post-separation showed only haploid propidium iodide peak (vertical lines) for all the epithelial cells:spermatozoa ratio tested (upper left (10:1), lower left (60:1), upper right (300:1), lower right (1500:1)).

CD52 staining was further tested for spermatozoa MACS separation from recovered mixed spermatozoa-epithelial cells samples. Samples were loaded with approximately 1e+6 epithelial cells and serially PBS-diluted sperm (up to more than 3000 times dilution factor). Samples were left to dry for several days before being restored, stained and separated by MACS technology (Miltenyibiotec, Bergisch Gladbach, Germany). Positive fraction of interest containing spermatozoa was further stained with propidium iodide and analyzed by flow cytometry (FIG. 5).

No diploid propidium iodide peak was observed for any of the epithelial cells:spermatozoa ratio tested. The podium iodide negative peak observed in all positive fractions corresponds to DNA-free debris most likely originating from the sample recovery procedure (cell debris, spermatozoa tails, swab debris).

Figure 6:
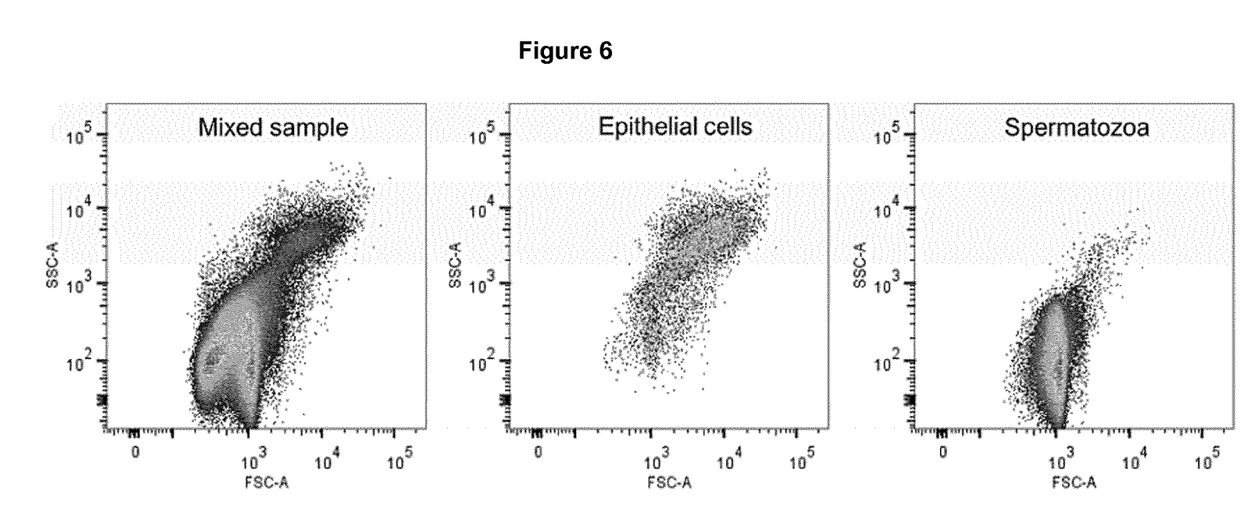
FIG. 6. Flow cytometry forward and side scatter signals for mixed samples, epithelial cells only or spermatozoa only samples. A clear different pattern is observed for single cells populations which provide a simple way for discrimination between both cell types. When recovered mixed samples are analyzed dual population is observed (along with a debris population on the dot plot lower left, due to the samples recovery procedure).

Flow cytometry forward and side scatter measurements give specific signals for both epithelial cells and spermatozoa (FIG. 6).

Figure 7:
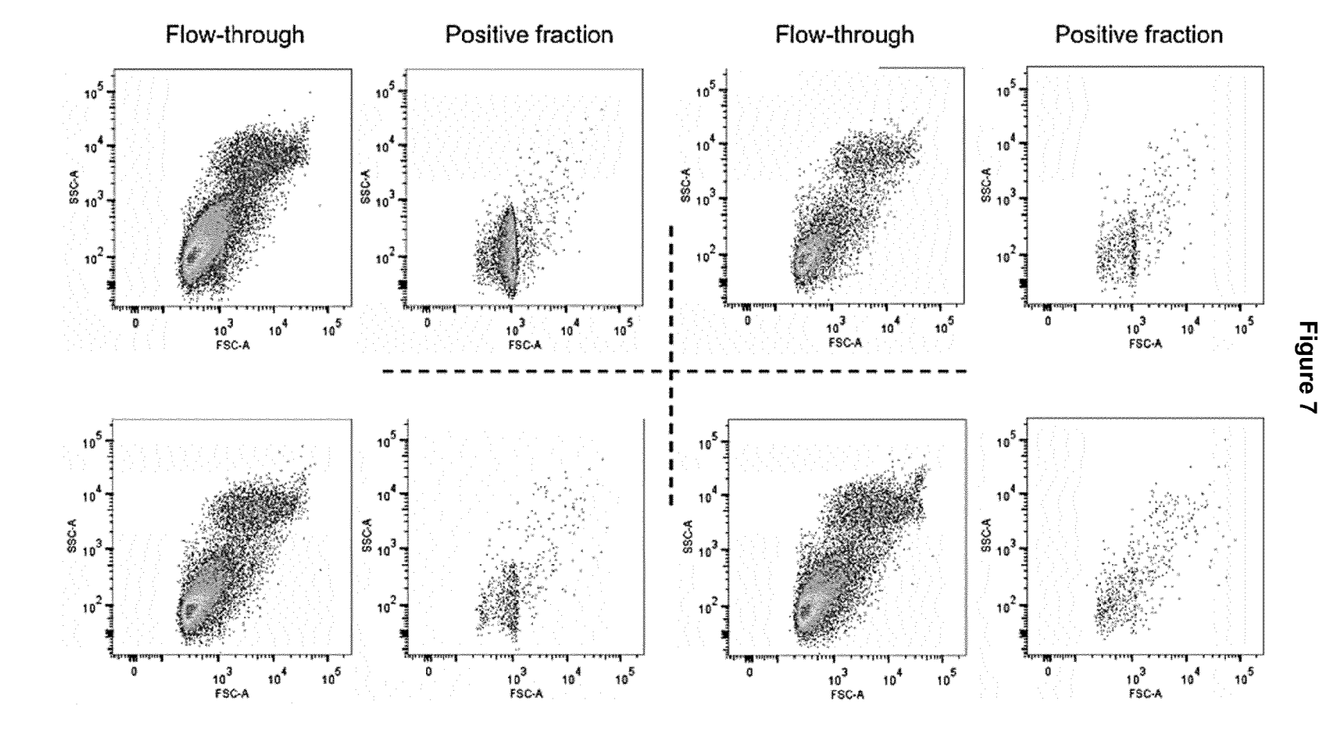
FIG. 7. Forward and Side scatter signals for flow-through and positive fraction post-MACS separation. Epithelial cells were only found in the flow-through along with the majority of cell debris (washed from the column). Spermatozoa were found in the positive fraction for all the epithelial cells: spermatozoa ratio tested (upper left (10:1), lower left (60:1), upper right (300:1), lower right (1500:1)).

Analyses of both flow-through and positive fraction post-MACS separation confirmed the efficient separation of the spermatozoa from the original mixture on the recovered samples. (FIG. 7).

Separation is Compatible with NGM Select Profile

Both positive fractions and flow-through post MACS separation were tested for STR (short tandem repeat) profiles of both female (epithelial cells) and male (spermatozoa) contributors.

Figure 8:
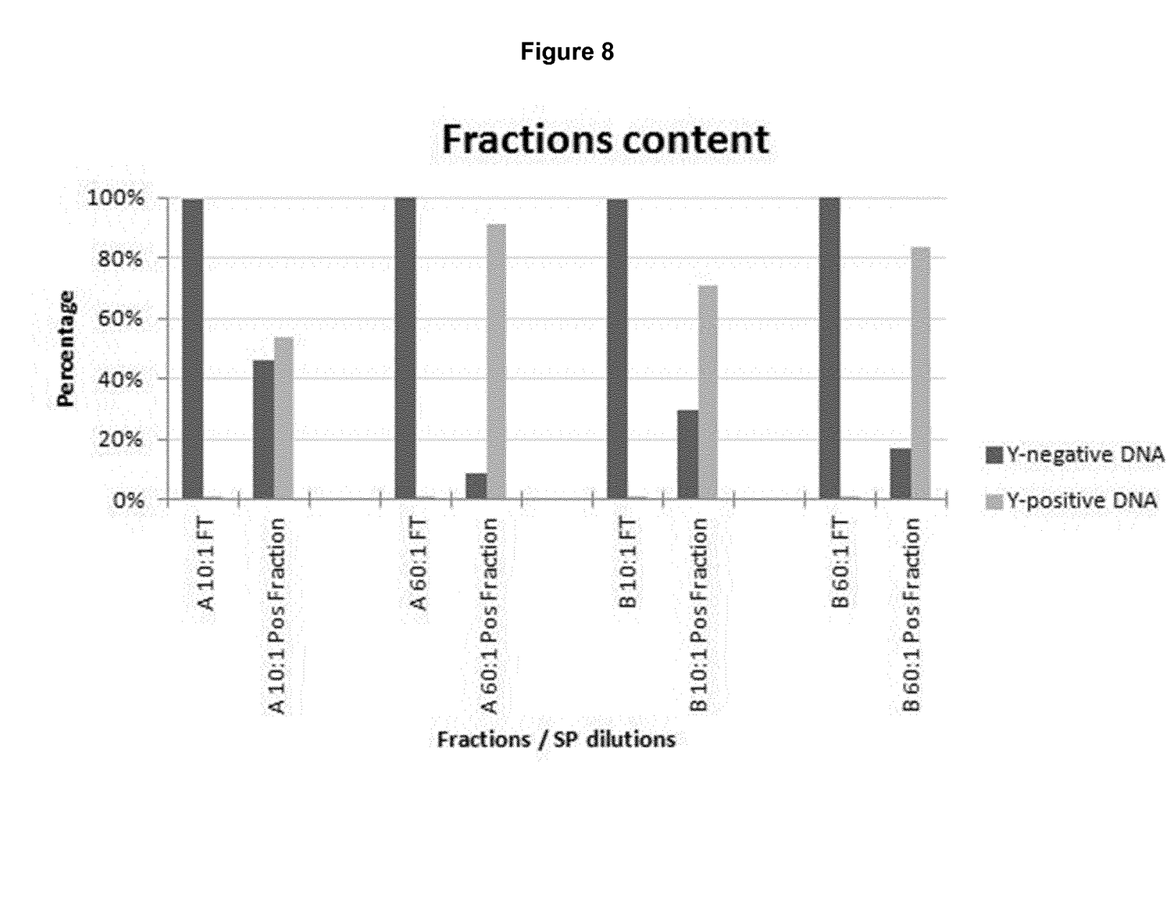
FIG. 8. Quantifiler Y positive and Y negative DNA distribution in the different fractions post-MACS separation. Quantifiler Y was used directly to measure Y chromosome contribution in the different fraction. Quantifiler Y was deduced from Quantifiler Human to measure non-Y contribution in the different fraction. All values were normalized to the total amount of measured DNA per fraction.

Quantifiler analyses of both human and Y DNA of the different fractions showed the absence of Y-positive DNA in the flow-through for the samples with the higher sperm concentration tested (10:1 and 60:1 epithelial cells:spermatozoa ratio). (FIG. 8).

Positive fractions showed both Y positive and Y negative DNA (as not every spermatozoa bears a Y chromosome). The ratio of Y-positive to Y-negative DNA in the flow-through does not always match a 50:50 distribution most likely due to stochastic effects with higher spermatozoa dilutions.

Figure 9:
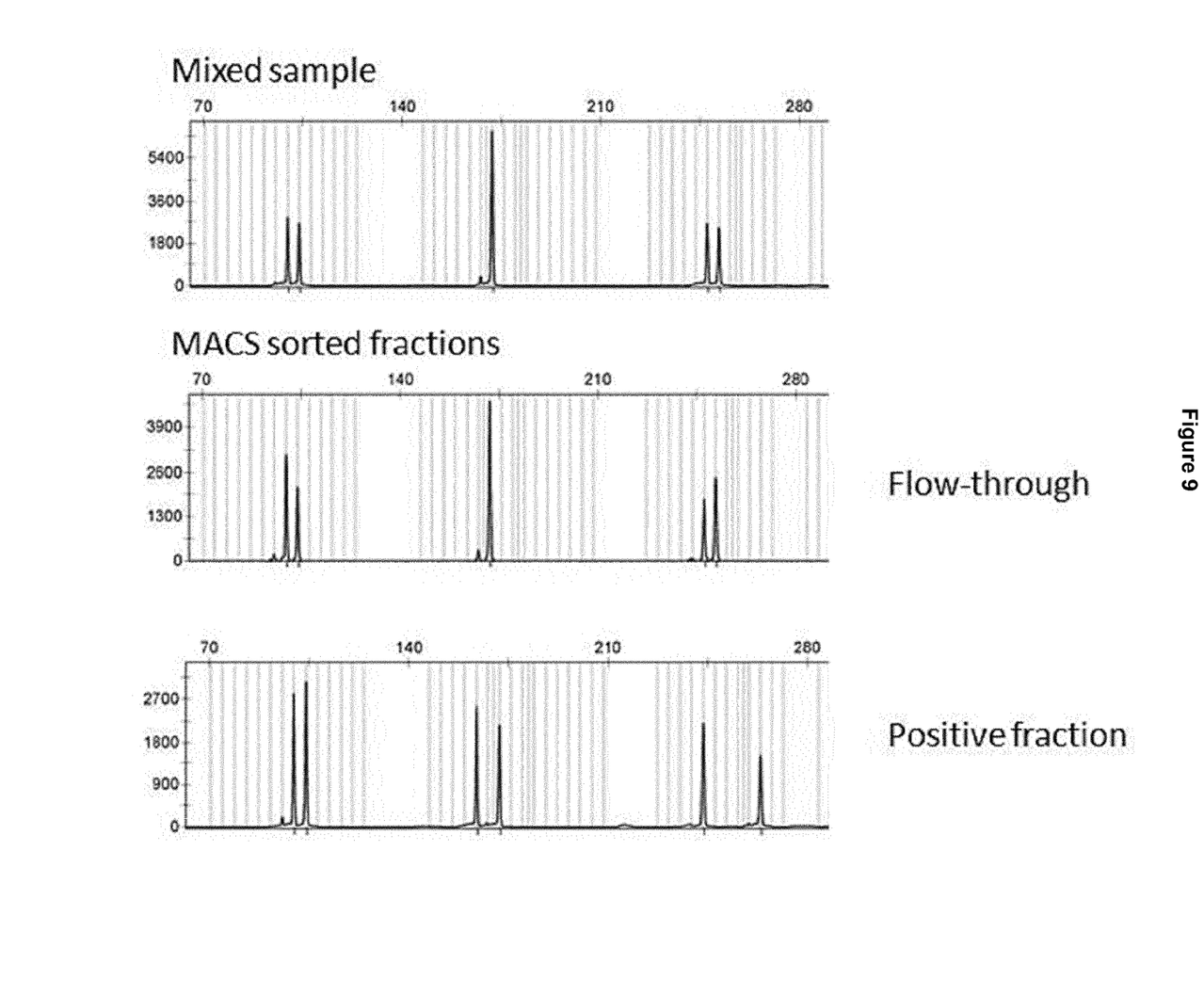
FIG. 9. NGM Select profile comparison before and after MACS separation. Only the female contributor profile is obtained in the original recovered non MACS sorted sample, whereas male profile becomes fully visible post-MACS separation, with no cross-contamination from the female contributor.

As expected in absence of separation, in recovered 60:1 epithelial cells:spermatozoa samples, the male contributor was masked by the female contributor profile (FIG. 9)

Figure 10:
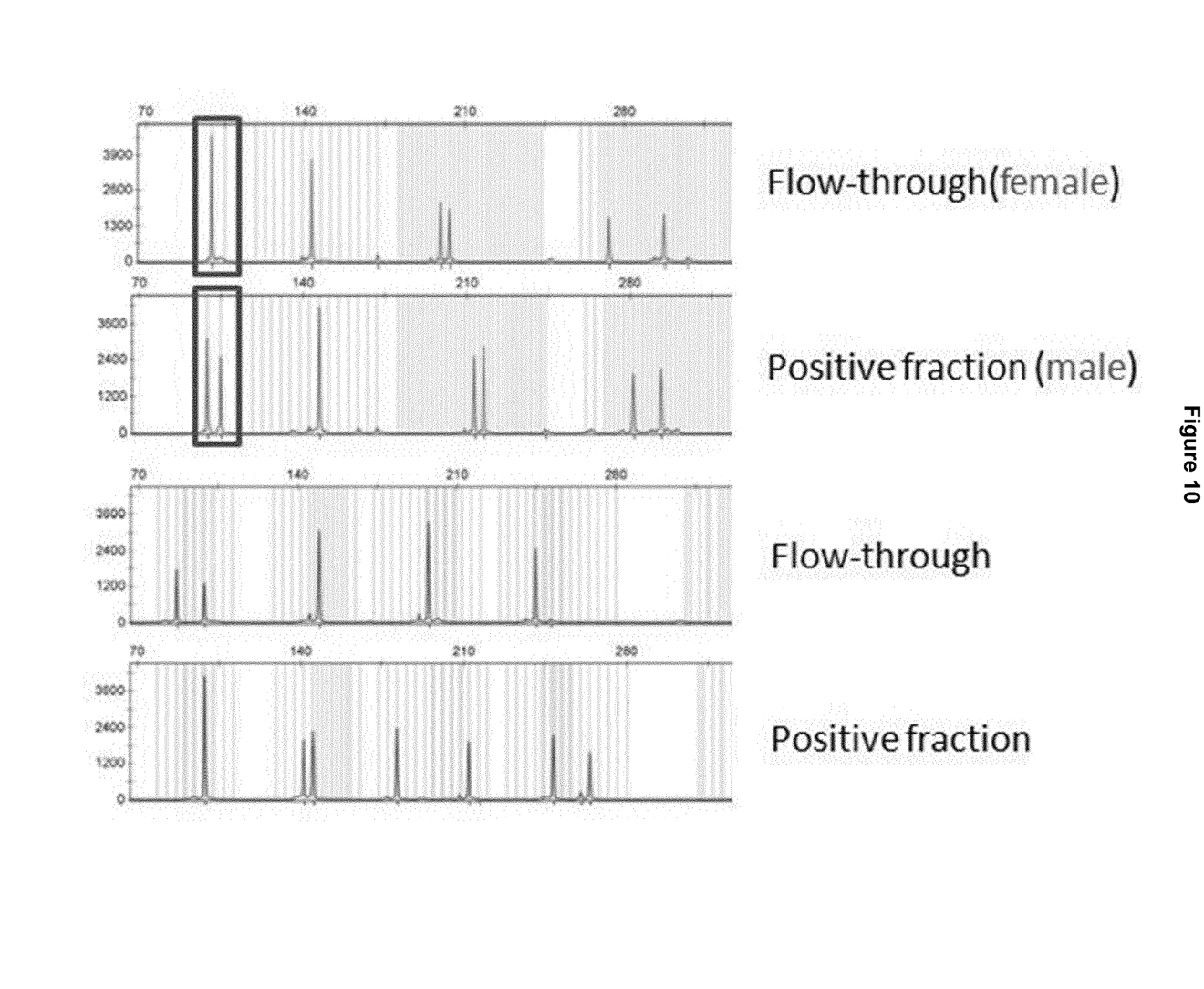
FIG. 10. NGM Select profile post-MACS separation. Clean male (positive fraction) and female (flow-through) profiles were obtained with no cross-contamination after separation from a 60:1 epithelial cells:spermatozoa recovered mixed sample. Purple box indicate amelogenin for male/female identification.

Clean single contributor profiles were obtained post-NGM Select amplification of the DNA extracted from both flow-through and positive fractions from an original recovered mixed samples (60:1 epithelial cells:spermatozoa). Female contributor profile was found in the flow-through and male contributor was found in the positive fraction (FIG. 10).

This proved that the separation procedure is compatible with the NGM Select STR amplification kit used to generate validated CODIS compatible profiles for identification. It also showed that the propidium iodide negative population observed in the positive fraction post-MACS separation does not interfere with a clean single contributor NGM Select profile, and thus does not contain free DNA originating from the epithelial cell contributor.

As expected, already in 60:1 epithelial cells:spermatozoa samples, non-MACS separated samples resulted in a female profile only, completely masking the male contribution, whereas once separated, a clean male profile was obtained.

Example 3

Proteinase K Influence on Spermatozoa Recovery

In order to increase the number of spermatozoa recovered from the swab, the recovery process can preferably be modified as follow:

The recovery buffer (i.e. PBS 2 mM EDTA) is complemented with 10 ng/ml proteinase K. Swab's cotton head are incubated for 30 minutes at 25° C. and 700 rpm on a thermomixer. The presence of proteinase K in the recovery buffer will also results in the lysis of most of the non-spermatozoa cells present in the cellular mixture being recovered, and therefore it is recommended to keep the supernatant post-recovery if the DNA profile of the non-spermatozoa cells contributor is required.

The recovery buffer containing the recovered material is then centrifuged (5 min at 13'000 rpm) to pellet spermatozoa, remaining epithelial cells (or other cell type present in the cellular mixture) and cell debris.

Supernatant is kept as mentioned above if the non-sperm contributor DNA profile is required.

The pellet is washed once with 150 ul PBS 2 mM EDTA and centrifuged 5 minutes at 13000 rpm. Washing buffer is discarded and spermatozoa are stained as previously described with a CD52 specific antibody for 15 minutes at 4° C. in the dark.

Spermatozoa are then washed once (optional) with 150 ul PBS 2 mM EDTA, centrifuged for 5 minutes at 13000 rpm and supernatant is discarded. Stained spermatozoa pellet is then resuspended in 300 ul of PBS 2 mM EDTA and run on the column.

Flow-through is collected in an eppendorf (and can be discarded). Magnetically bound spermatozoa are washed twice on the column by adding 500 ul PBS 2 mM EDTA.

The column is then removed from the magnet and the spermatozoa, placed onto a new clean eppendorf and 700 ul PBS 2 mM EDTA are added in the column. Spermatozoa are then flushed out of the column by applying pressure on a plunger within the column.

The collected spermatozoa are then centrifuged again (5 minutes at 13000 rpm) prior to lysis to increase the final spermatozoa's DNA concentration.

Cell number recovery can be established by FACS counting, or by DNA quantification.

Increasing proteinase K concentration from 10 to 100 ng/ml increased the ratio of recovered spermatozoa versus epithelial cells as it decreased the number of remaining intact epithelial cells drastically. With less intact epithelial cells remaining in the cell pellet post cell recovery, there's very little risk remaining of clogging the column while separating the spermatozoa from the other cells types in presence.

The invention claimed is:

1. A method for separating spermatozoa according to the specific marker CD52 (Human epididymal secreted protein) expressed on their surface from a plurality of cells contained, in a dry state, on an inert substrate, which method comprises the steps of:
   i) obtaining the plurality of cells contained on the inert substrate,
   ii) contacting said plurality of cells with a serum-free buffer comprising 1× phosphate buffered saline (PBS) and about 2-20 mM of EDTA, at about 10-30° C. for 10-45 minutes and exposing the plurality of cells to at least one magnetic particle under conditions effective to allow direct or indirect coupling of the magnetic particle to the specific marker CD52 expressed on the surface of the spermatozoa,
   iii) recovering the plurality of cells, and
   iv) separating the spermatozoa that are coupled to the magnetic particle from the cells not coupled to the magnetic particle.

2. The method of claim 1, wherein the serum-free buffer further comprises about 10-200 ng/ml of proteinase K.

3. The method of claim 1, wherein the serum-free buffer comprises about 2-10 mM of EDTA.

4. The method of claim 1, wherein said plurality of cells is contacted with the serum-free buffer at 25° C. for 30 minutes.

5. The method of claim 1, wherein the cells of the plurality of cells contained on an inert substrate are selected from the group consisting of spermatozoa, epithelial cells, vaginal cells, buccal epithelial cells, white blood cells and red blood cells.

6. The method of claim 1, wherein the method further comprises a step of washing the plurality of cells contacted with the serum-free buffer with a washing buffer before exposing said plurality of cells to the at least one magnetic particle.

7. The method of claim 6, wherein the washing buffer consists of 1× PBS and about 2-20 mM EDTA.

8. The method of claim 1, wherein steps i) and ii) can be repeated several times.

9. The method of claim 1, wherein the conditions effective to allow direct coupling of the magnetic bead to the specific marker CD52 expressed on the surface of the spermatozoa comprise the step of contacting the plurality of cells obtained from said inert substrate with a serum-free buffer comprising 1× PBS and about 2-20 mM EDTA during 5 to 30 minutes at a temperature between about 4° C. to 25° C. and containing at least one magnetic particle labeled with a binding partner that specifically binds to the marker CD52 expressed on the surface of the spermatozoa, optionally under agitation.

10. The method of claim 9, wherein the EDTA concentration is from about 2-10 mM EDTA.

11. The method of claim 9, wherein the binding partner that specifically binds to the marker CD52 expressed on the surface of the spermatozoa is conjugated with a label moiety which is detectable either directly or indirectly.

12. The method of claim 9, wherein the binding partner that specifically binds to the marker CD52 expressed on the surface of the spermatozoa is an antibody or an antigen-binding portion thereof.

13. The method of claim 12, wherein the antibody is selected from the group consisting of a polyclonal or a monoclonal antibody, a chimeric antibody, a bispecific antibody, a hapten and an antibody fragment.

14. The method of claim 1, wherein the conditions effective to allow indirect coupling of the magnetic particle to the specific marker CD52 expressed on the surface of the spermatozoa comprise the steps of:
i) first contacting the plurality of cells obtained from said inert substrate with a serum-free buffer comprising 1× PBS and about 2-20 mM EDTA further containing a binding partner to the specific marker for 5 to 30 minutes at a temperature between 4° C. to 25° C., optionally under agitation, thereby labeling the cells of interest with said binding partner, wherein said binding partner is biotinylated, unconjugated or conjugated with a label moiety, and
ii) contacting the plurality of cells of step i) containing the spermatozoa coupled with the binding partner, with a magnetic particle comprising a molecule specifically recognizing the binding partner, the biotin or the label moiety conjugated to said binding partner.

15. The method of claim 14, wherein the binding partner that specifically binds to the marker CD52 expressed on the surface of the spermatozoa is an antibody or an antigen-binding portion thereof.

16. The method of claim 14, wherein the molecule specifically recognizing the binding partner, the biotin or the label moiety conjugated to said binding partner is an antibody or an antigen-binding portion thereof.

17. The method of claim 1, wherein the step of separating the cells that are coupled to the magnetic particle from those not coupled to the magnetic particle is performed by a magnetic separation technique in a source of magnetic field.

18. The method of claim 17, wherein the magnetic separation technique consists of high gradient magnetic separation (HGMS).

19. The method of claim 1, wherein the cells are applied to a column within a separation device.

20. The method of claim 1, wherein the magnetic particle is in a size range of about 5 to 200 nm.

21. The method of claim 1, wherein said at least one magnetic particle is labeled with the antibody or the antigen-binding portion thereof through a linker.

22. A method for selectively enriching cells in spermatozoa according to the specific marker CD52 (Human epididymal secreted protein) expressed on their surface from a plurality of cells contained, in a dry state, on an inert substrate, which method comprises the steps of:
i) obtaining the plurality of cells contained on the inert substrate,
ii) contacting said plurality of cells with a serum-free buffer comprising 1× PBS and about 2-20 mM of EDTA, at about 10-30° C. for 10-45 minutes and exposing the plurality of cells to at least one magnetic particle under conditions effective to allow direct or indirect coupling of the magnetic particle to the specific marker CD52 expressed on the surface of the spermatozoa,
iii) recovering the plurality of cells, and
iv) separating the spermatozoa that are coupled to the magnetic particle from the cells not coupled to the magnetic particle.

\* \* \* \* \*